US00PP14926P3

(12) United States Plant Patent
Heims et al.

(10) Patent No.: US PP14,926 P2
(45) Date of Patent: Jun. 22, 2004

(54) ZANTEDESCHIA PLANT NAMED 'EDGE OF NIGHT'

(50) Latin Name: *Zantedeschia hybrid*
Varietal Denomination: Edge of Night

(75) Inventors: Daniel M. Heims, Portland, OR (US); Frank Patterson, West Linn, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 100 days.

(21) Appl. No.: 10/222,546

(22) Filed: Aug. 15, 2002

(65) Prior Publication Data

US 2004/0034893 P1 Feb. 19, 2004

(51) Int. Cl.[7] ..... A01H 5/00
(52) U.S. Cl. ..... Plt./356
(58) Field of Search ..... Plt./356, 263

*Primary Examiner*—Bruce R. Campell
*Assistant Examiner*—Michelle Kizilkaya
(74) *Attorney, Agent, or Firm*—Klarquist Sparkman, LLP

(57) ABSTRACT

A new and distinct Zantedeschia plant named 'Edge of Night', having striking, extremely dark purple, almost black, spathes, leaf margins and petioles.

1 Drawing Sheet

Botanical name: Zantedeschia hybrid.
Variety denomination: 'Edge of Night'.
Common name: Calla Lily.

The present invention relates to a new and distinct cultivar of Zantedeschia hybrid and given the cultivar name 'Edge of Night'. Zantedeschia is in the family Araceae.

This new cultivar was discovered in a large shipment Zantedeschia 'Schwarzwalder' (U.S. Plant Pat. No. 11,001). It is thought to be a spontaneous mutation. It was found by Frank Patterson in West Linn, Oreg.

This plant is characterized by the following:

1. Extremely dark purple, almost black, flowers or spathe.
2. Very dark petioles and leaf margins.
3. Leaves spotted white and pink.
4. Excellent vigor.

This new cultivar has been reproduced only by asexual propagation (division and tissue culture). Each of the progeny exhibits identical characteristics to the original plant. Asexual propagation by tissue culture using standard micropropagation techniques with side shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two year old plant in flower grown in a one gallon container in the greenhouse in Canby, Oreg.

DETAILED PLANT DESCRIPTION

The following is a detailed description of the new Zantedeschia cultivar based on observations of two-year-old specimens grown in the greenhouse in a one-gallon container in Canby, Oreg. The color descriptions are all based on The Royal Horticultural Society Colour Chart.

Botanical classification: Zantedeschia hybrid.
Cultivar name: 'Edge of Night'.

Plant:
- *Type*.—Herbaceous perennial.
- *Form*.—Rhizomatous, erect, with 3 to 4 leaves per corm.
- *Hardiness*.—U.S.D.A. Hardiness Zones 8 to 10.
- *Size*.—50 to 65 cm to the top of the leaves and 30 to 40 cm wide.

Corm:
- *Size*.—5 by 7 cm wide.

Leaf:
- *Type*.—Simple.
- *Arrangement*.—Basal.
- *Number*.—12 on average.
- *Shape*.—Lanceolate to ovate.
- *Blade size*.—21 to 29.5 cm long and 12 to 15 cm wide.
- *Venation*.—One main vein with parallel lateral veins or penni-parallel.
- *Margins*.—Entire, undulate.
- *Apex*.—Obtuse to candate.
- *Base*.—Sagittate.
- *Texture*.—Leathery, thick.
- *Vestiture*.—Glabrous on top and pubescent on bottom.
- *Surface*.—Glossy.
- *Petiole*.—Size — 42 cm long and 7 mm wide. Shape in cross section — Oval with one end flattened. Vestiture — Glabrous. Color — Dark maroon, Greyed Purple 187A. Aspect — Petioles rise at 15 degree angle from the vertical.
- *Leaf color*.—Abaxial — Deep green, Green 137A, with linear shaped white spots, White 155B, or sometimes pink spots Greyed Purple 185C. Leaf margins are dark maroon, Greyed Purple 187A. Adaxial — Green color and spot color are the same as above. The veins at the leaf base and the margin are very dark maroon, between Black 202A and Greyed Purple 187A.

Inflorescence:
- *Type*.—Long stalked spathe.
- *Peduncle*.—Height — 60 to 75 cm tall. Width — 1 cm. Texture — Smooth, rubbery. Color — Dark maroon, Greyed Purple 187A but blacker.
- *Bloom time*.—Spring.

Spathe:
*Shape*.—Funnelform, overlapping by 3 cm.
*Size*.—11 cm deep and 10 cm wide.
*Apex*.—Caudate.
*Margins*.—Entire.
*Color*.—Very dark maroon, between Greyed Purple 187A and Black 202A.
*Lastingness*.—One month.
Spandix:
*Size*.—7 cm long and 1 cm wide at the widest point.
*Color*.—Greyed Purple 187A.
Fragrance: None.
Lastingness: About 3 weeks on the plant.
Use: Best used as a container plant.
Fruit: None produced, plant sterile.
Seed: None produced, plant sterile.
Disease: None observed on plants grown commercially in Canby, Oreg.

COMPARISONS

Compared to the parent plant, Zantedeschia 'Schwarzwalder' (U.S. Plant Pat. No. 11,011) with green leaf margins, green petioles, and green leaf veins, Zantedeschia 'Edge of Night' has much darker flowers and is dark on the leaf margins, petioles, and leaf veins.

I claim:

1. A new and distinct variety of Zantedeschia plant substantially as shown and described.

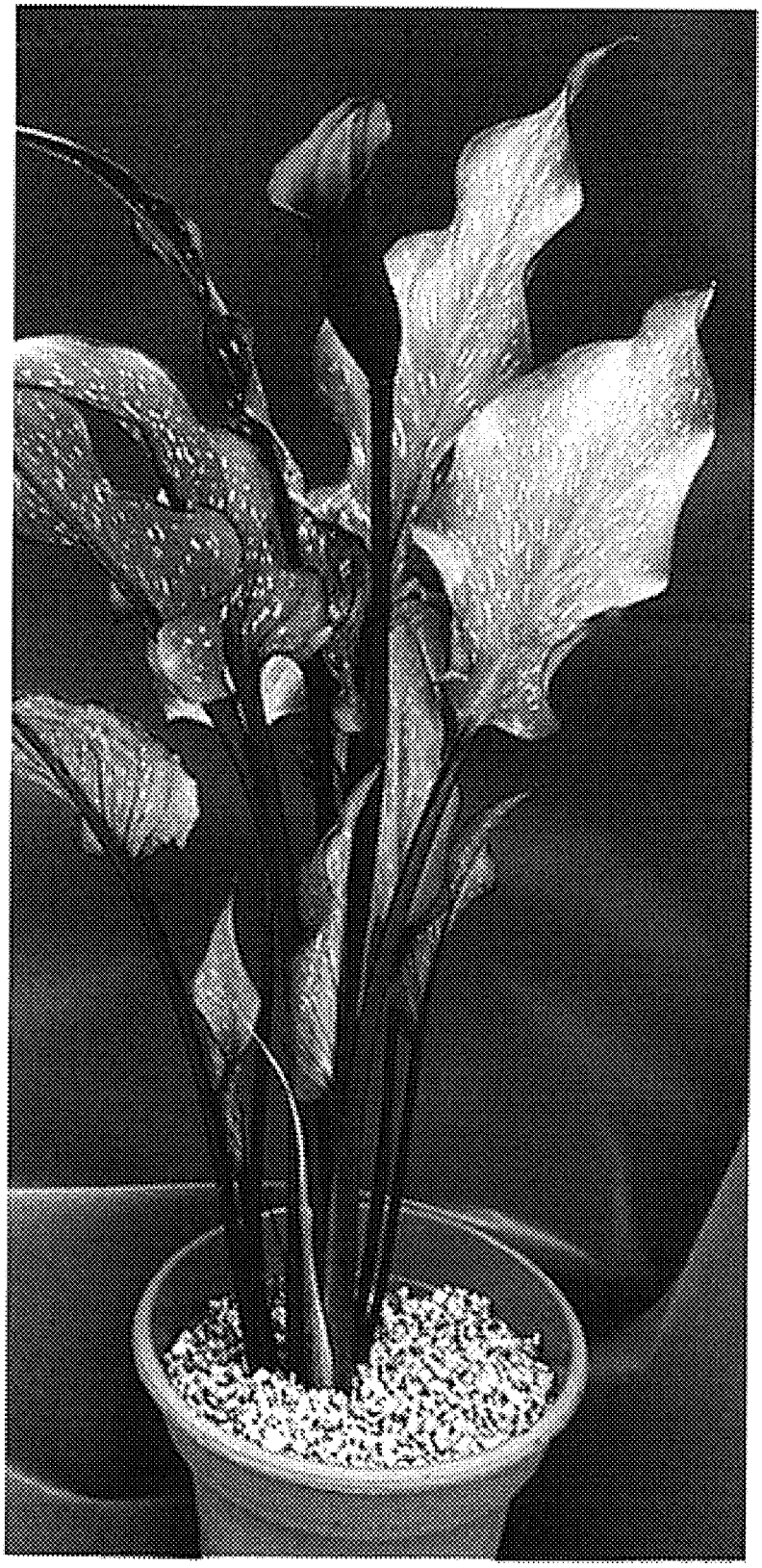

* * * * *